United States Patent [19]

Wiederkehr

[11] 4,320,236

[45] Mar. 16, 1982

[54] ETHYNYLATION

[75] Inventor: Hermann Wiederkehr, Flüh, Switzerland

[73] Assignee: Hoffmann-La Roche Inc., Nutley, N.J.

[21] Appl. No.: 188,640

[22] Filed: Sep. 19, 1980

[30] Foreign Application Priority Data

Oct. 19, 1979 [CH] Switzerland .................. 9419/79

[51] Int. Cl.$^3$ .............................................. C07C 33/28
[52] U.S. Cl. .................................................. 568/813
[58] Field of Search ........................................ 568/813

[56] References Cited

U.S. PATENT DOCUMENTS

| | | | |
|---|---|---|---|
| 2,425,201 | 8/1947 | Oroshnik et al. | 568/813 |
| 3,082,260 | 3/1963 | Tedeschi | 568/813 |
| 3,283,014 | 11/1966 | Balducci et al. | 568/813 |
| 3,557,220 | 1/1971 | Bach et al. | 568/874 |
| 3,576,889 | 4/1971 | Martin et al. | 568/813 |
| 3,709,946 | 1/1973 | Tedeschi et al. | 568/813 |

OTHER PUBLICATIONS

Rutledge, "Acetylenic Compounds", Reinhold Book Corp., N.Y. (1968), pp. 166–196.
Tedeschi et al. "J. Organic Chemistry" vol. 34, (1969), pp. 435–438.
Beumel et al. "J. Organic Chemistry" vol. 28 (1963), pp. 2775–2779.
Martin et al., "J. Organic Chemistry" vol. 33 (1968), pp. 778–780.
Oroshnik et al. "J. American Chemical Soc." vol. 71 (1949), pp. 2062–2065.

*Primary Examiner*—Werren B. Lone
*Attorney, Agent, or Firm*—Jon S. Saxe; George M. Gould; William H. Epstein

[57] ABSTRACT

A process for the ethynylation of alpha, beta-unsaturated ketones to produce compounds containing the tertiary acetylenic alcohols which are useful as intermediates in carotenoids.

15 Claims, No Drawings

ETHYNYLATION

BACKGROUND OF INVENTION AND STATEMENT OF PRIOR ART

The process for ethynylating alpha,beta-unsaturated ketones for producing tertiary acetylenic alcohols is old and well known. See U.S. Pat. No. 3,709,946, Jan. 9, 1973, U.S. Pat. No. 3,082,260, Mar. 19, 1963, and U.S. Pat. No. 3,283,014, Nov. 1, 1966. A review concerning the hitherto used ethynylation reactions is given to T. F. Rutledge, Acetylenic Compounds, Reinhold Book Corporation (1968), p. 46-84 and 166-196. According to the classical process, ethynylation is carried out with sodium acetylide in liquid ammonia, as well as with calcium or lithium acetylide U.S. Pat. No. 2,425,201; W. Oroshnik et al., J. Amer. Chem. Soc. 71 (1949) 2062-2065. However, in these cases, alpha,beta-unsaturates ketones are generally obtained only small yields, since these ketones partially polymerize in ammonia. On the other hand, the monolithium acetylide spontaneously decomposes upon isolation from ammonia to dilithium acetylide (lithium carbide) and acetylene [R. J. Tedeschi et al., J. Org. Chem. 34 (1969) 435-438]. The high yields published for a process with the monolithium acetylide-ethylene-diamine complex in an organic solvent [O. F. Beumel et al., J. Org. Chem. 28 (1963) 2775-2779] could not be reproduced [K. R. Martin et al., J. Org. Chem. 33 (1968) 778-780], since the ethylenediamine liberated in the reaction caused self-condensation and polymerization of the alpha,beta-unsaturated ketones.

A newer ethynylation process, in which alkali metal acetylides are stabilized in ethers with non-basic compounds (U.S. Pat. No. 3,576,889), provides to some extent very good yields. However, this procedure is poorly suited to large-scale technical syntheses, since foreign substances in large-scale processes frequency cause trouble. Furthermore, these foreign substances must subsequently be further separated. Moreover, expensive lithium amide must be employed in the preferred embodiment of this process.

SUMMARY OF INVENTION

The process in accordance with the invention is characterized in that a ketone of the formula $$R-CH=CH-CO-CH_3 \qquad I$$

wherein R is hydrogen or an aliphatic hydrocarbon or aromatic hydrocarbon, is ethynylated at a temperature of below about 30° C. with a suspension of the monolithium acetylide-ammonia complex in an inert organic solvent, and if desired, a thus-obtained compound of the general formula $$R-CH=CH-C(OLi)(CH_3)-C\equiv CH \qquad II$$

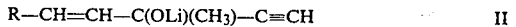

wherein R is as above, is hydrolyzed by conventional procedures to a compound of the formula $$R-CH=CH-C(OH)(CH_3)-C\equiv CH \qquad III$$

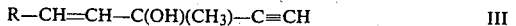

wherein R is as above.

The invention is further directed to a specific monolithium acetylide ammonia complex composition which can be used to affect this ethynylation and to methods for its manufacture. In accordance with this invention, ethynylation is carried out in high yields when the monolithium acetylide ammonium complex composition suspended in the organic solvent medium contains 70% to 120% equivalents of ammonia per equivalent of lithium.

The process in accordance with the invention now enables, by simple process conditions, the stabilization of the lithium acetylide-ammonia complex in an inert organic solvent. At the same time, the polymerization of the ketone is kept at a minimum and a very high yield (94-99%) of ethynyl carbinols of formula III is obtained. The process is technically readily usable and inexpensive. With the use of dry organic solvent and reaction components, excess lithium can be reduced, and moreover, because of the less salt and resin separation as well as by working-up of the solvent and of the separated lithium salt, the environmental problems are considerably reduced.

DETAILED DESCRIPTION

The reaction of the carbonyl group of the ketone of formula I is largely independent on the nature of the substituent R, if this substituent has no reactive group. The hydrocarbons defined by R can be unsubstituted or substituted with unreactive substituents such as lower alkoxy or lower alkyl.

R can be hydrogen or any aliphatic or aromatic hydrocarbon which can be unsubstituted or substituted. Among the preferred groups for R are alkyl, alkenyl, alkynyl, cycloalkyl, cycloalkenyl, aryl, aryl-lower alkyl, aryl-lower alkenyl, cycloalkyl-lower alkyl, cycloalkyl-lower alkenyl, cycloalkenyl-lower alkyl and cycloalkenyl-lower alkenyl. In accordance with this preferred embodiment, the aforementioned aryl, cycloalkyl or cycloalkenyl groups can be unsubstituted or substituted in at least one position with one or more substituents selected from the group consisting of lower alkyl or lower alkoxy.

The term "aliphatic hydrocarbon" embraces open chain aliphatic and cycloaliphatic hydrocarbons as well as substituents containing both aliphatic and cycloaliphatic moieties. In accordance with a preferred embodiment of this invention, R is either a alkyl radical containing 1 to 20 carbon atoms such as methyl, ethyl, isopropyl, n-propyl, octadecyl, 6-methyl-10-ethyl-hexadecyl, etc. The term alkenyl designates alkenyl groups having at least one olefinic double bond and containing from 2 to 20 carbon atoms such as vinyl, allyl, 5-octenyl, 2,3-dimethyl-4-octenyl, 8-hexadecenyl, 5,6-dimethyl-7-hexadecenyl, 5,6-dimethyl-7-hexadecenyl, etc. The term alkynyl embraces alkynyl groups having at least one triple bond and containing from 3 to 20 carbon atoms such as propynyl, 3,7-dimethyl-5-octynyl, 6-heptadecynyl, etc.

Cycloalkyl groups which are designated by R generally contain from 3 to 8 carbon atoms, such as cyclopropyl, cyclohexyl and the like. The cycloalkenyl groups designated by R contain from 3 to 8 carbon atoms, such as cyclopropenyl, cyclohexenyl, etc. The term "aryl" designates aromatic, monocyclic or bicyclic residues which can if desired contain a hetero atom in the ring. Among the preferred hetero atoms are sulfur, oxygen and nitrogen. The preferred aromatic residues are phenyl, naphthyl, and pyridinyl and the like.

The term lower alkyl designates saturated aliphatic hydrocarbon radical containing from 1 to 7 carbon atoms such as methyl, ethyl, n-propyl, isopropyl, etc. The term "lower alkenyl" designates lower alkenyl radicals containing from 2 to 7 carbon atoms such as vinyl allyl, etc. The term "lower alkoxy" designates lower alkoxy radicals containing from 1 to 7 carbon atoms such as methoxy, isopropoxy, ethoxy, etc.

When the aryl, cycloalkyl or cycloalkenyl groups are substituted, they can be preferably substituted in at least one portion, particularly from one to four positions with either lower alkyl or lower alkoxy substituents or combinations of lower alkyl or lower alkoxy substituents.

Especially preferred substituents designating R are hydrogen, 4-methoxy-2,3,6-trimethylphenyl and 2,6,6-trimethyl-1-cyclohexen-1-yl.

The ethynylation of a ketone of general formula I is effected by addition of the ketone to a suspension of the monolithium acetylide-ammonia complex in an inert organic solvent at a temperature of below about 30° C. Preferably, a temperature between −30° and 20° C., especially between −20° and 10° C. is used. The reaction is conveniently performed by the slow and uniform addition of a pre-cooled ketone solution. Preferably, the reaction is carried out with continuous acetylene saturation of the reaction mixture. The ketone solution is preferably manufactured in the same solvent as the acetylide suspension. Ethers and aromatic hydrocarbon compounds, such as diethyl ether, di-n-propyl ether, diisopropyl ether, dioxane, tetrahydrofuran, benzene, toluene and the like are preferred inert organic solvents. Toluene and diethyl ether are especially preferred.

The hydrolysis of a compound of general formula II can be effected in a manner known per se, e.g. with sulfuric acid, acetic acid, water, ammonium chloride and the like. Any of the conditions in hydrolyzing with these agents can be used in this procedure.

The reaction of this invention is carried out in the presence of a monolithium acetylide-ammonia complex composition suspended in the inert organic solvent medium. In general, this complex of formed by utilizing a solution of a lithium acetylide-ammonia complex in liquid ammonia through solvent exchange. In accordance with a preferred embodiment of this invention, suspension of such a complex composition wherein the suspension contains 70 to 120% equivalents of ammonia, preferably 80 to 99% equivalents of ammonia, per equivalent of lithium is used in carrying out this reaction. This ratio of ammonia to lithium in the suspension produces the compound of formula II in very high yields. If the ratio of equivalents of ammonia to lithium in this suspension is below this aforementioned range, then the stabilization of the acetylide is no longer achieved and the complex contained in the suspension is subject to break down during the ethynylation reactions. On the other hand, if this ratio is too large, then the dissolved ammonia can, in some cases such as in the case where 3-buten-2-one is used as a starting material, cause increased polymerization of the ketone during the ethynylation reaction. Furthermore, in carrying out the reaction of this invention according to the preferred embodiment, high yields are obtained when the amount of ammonia present in the reaction medium is no greater than the aforementioned ratio. Therefore, in accordance with a preferred embodiment of this invention, there should be no additional ammonia present in the reaction medium.

The formation of the suspension of monolithium acetylide ammoninia complex containing from about 70 to 120% equivalents of ammonia per equivalent of lithium is carried out by utilizing monolithium acetylide, dilithium acetylide or mixtures thereof dissolved in liquid ammonia as a starting material through solvent exchange with an inert organic solvent. In accordance with this procedure, when this solvent exchange is carried out, this results in characteristic temperature profile with constant heat production, which makes possible a simple reaction control and which is important especially for the adjustment of the remaining ammonia content to the aforementioned levels. In carrying out the solvent exchange, the ammonia solvent is evaporated from the reaction medium while adding an inert organic solvent. This solvent exchange is continued for a period of time sufficient to reach a range in which the temperature of the reaction mixture remains approximately constant.

In carrying out the solvent exchange to produce the preferred suspension of the complex containing the aforementioned ratio of ammonium to lithium, a monolithium acetylide or dilithium acetylide or mixtures thereof dissolved in liquid ammonia is used as the starting material. The solvent exchange to produce the suspension of the lithium-acetylide ammonia complex composition is conveniently effected by evaporation of the ammonia and during this evaporation holding level in the reaction vessel approximately constant by addition of the inert organic solvent. If the liquid ammonia is evaporated through a condenser regulated at about −30° to −20° C., then a reuse is also possible with an exchange for a relatively low boiling organic solvent. During the ammonia evaporation there occurs, starting from about −40° to −30° C., firstly a slow and then a large rise of the internal temperature of the reaction medium. Subsequently, there follows a range in which the temperature remains approximately constant (temperature plateau). The level of this temperature plateau depends on the solvent and on the concentration of the mono- or dilithium acetylide in the medium. When the plateau temperature is reached, it is further heated until the internal temperature again begins to rise and the, if necessary, acetone-free acetylene gas is conducted into the reaction mixture. The acetylene gas is used to convert the dilithium acetylide which may be present in the starting material to monolithium acetylide. The internal temperature at the end of the temperature plateau should rise only a few degrees preferably from 2° to 7° C. above the plateau temperature, since thereby the residual ammonia content and therewith the stability of the lithium acetylide is influenced. As an alternative, the acetylene introduction can also be commenced already at the temperature plateau. Insofar as the acetylide is already present completely as the monolithium acetylide, the acetylene introduction can be forgone. It is, however, in most cases advantageous if the subsequent ethynylation reaction is carried out with continuous saturation of the reaction solution with acetylene. In the reaction with acetylene, the temperature should not rise above about 30° C., preferably not above about 10° C.

It is presumed that the monolithium acetylide-ammonia complex described herein is the monoammoniate (M. Corbellini et al., Chim. e Ind. (Milano) 42 (1960) 251–254; E. Masdupuy, Ann. chim. (Paris) 2 (1957) 527–586, Chem. Abstr. 52 (1958) 2627d) of the formula

$$LiC\equiv CH.NH_3 \qquad\qquad IV$$

A blank test of the solvent exchange without lithium acetylide shows that the temperature plateau is produced by the presence of the acetylide. A possible explanation would be, in the case of the monolithium acetylide, the reaction

whereby on the basis of the titration results x is probably 2.

An alternative to the above-described manufacture of the monolithium acetylide-ammonia complex is the reaction of lithium amide with acetylene in an inert organic solvent. The reaction is conveniently carried out so that firstly lithium amide is suspended in an inert organic solvent and then acetone-free acetylene is conducted into this suspension. The temperature of the reaction mixture should thereby not be higher than the temperature which was measured in the case of the same solvent and same concentration at the end of the above-described solvent exchange, i.e. it should not rise above about 30°C., preferably not above about 10° C.

In the manufacture of the monolithium acetylide-ammonia complex there is conveniently used the same inert organic solvent as in the subsequent ethynylation. The first embodiment, i.e. the solvent exchange on a lithium acetylide-ammonia solution and, if necessary, reaction with acetylene, is preferred.

The manufacture of the lithium acetylide-ammonia solution is known per se. It can be effected by dissolution of lithium, lithium amide, dilithium acetylide, lithium hydride, butyl lithium or other suitable lithium salts, preferably lithium or lithium amide, in liquid ammonia and, if necessary, reaction with acetylene. It is, however, also possible to add the lithium or lithium salt to a saturated solution of acetylene in liquid ammonia. The acetylene introduction can be discontinued at the grey point, at the white point or at an optional point therebetween, depending on whether one desires to undertake the solvent exchange on the dilithium acetylide, on the monolithium acetylide or on a mixture of the two. Conveniently, acetylene is conducted in for at least several minutes beyond the grey point. Since, furthermore, upon solvent exchange a partial decomposition of the monolithium acetylide to the dilithium acetylide can appear, there is likely to be present immediately after the solvent exchange mainly a mixture of the mono- and dilithium acetylide.

EXAMPLE 1

A solution, pre-cooled to ca −50° C., of 100 g of 3-buten-2-one (purity 98.7%, water content 0.4%) in 100 ml of diethyl ether is added uniformly within 30 minutes to a suspension of the monolithium acetylide-ammonia complex in diethyl ether with continuous saturation of the reaction mixture with acetylene. After completed addition, the mixture is left to react for a further 5 minutes.

Subsequently, the reaction mixture is allowed to flow within 20 minutes and while stirring into 390 ml of 30% sulfuric acid so that the pH-value is always below 7 and the temperature does not rise above −5° C. The mixture is adjusted with sodium hydroxide to a pH-value of 6.0–6.5. Thereafter, the solution is filtered, the residue is washed with a little ether and the ether phase is dried over sodium sulfate. The filter residue contains salts and less than 0.1 g of polymerizate. The distillation of the ether phase with a Vigreux column finally gives 127.35 g of 3-methyl-4-penten-1-yn-3-ol and 4.4 g of distillation residue. Yield: 94.1% (based on lithium 88.5%).

The suspension of the monolithium acetylide-ammonia complex in diethyl ether is manufactured as follows:

10.5 g of lithium (purity 99%) are dissolved in 500 ml of liquid ammonia in a reaction vessel with reflux condenser (ca −70° C.) while stirring at −40° C. within 20 minutes. Subsequently, acetylene (ca 4 l/min.) is conducted into the solution at the same temperature through an immersion tube. After about 15 minutes a color change from blue-black to light grey (grey point) takes place. The acetylene introduction can be continued for 5 minutes beyond the grey point. Thereafter, the temperature in the reflux condenser is regulated to ca −20° C., ammonia is evaporated off and the distilled-off amount is continuously replaced by diethyl ether (total 625 ml). When the plateau temperature of ca 5° C. is reached, the mixture is furthermore heated with a mantle temperature of ca 20° C. until the internal temperature again begins to rise. After reaching the end temperature of ca 7°–8° C., the total volume of the reaction mixture should again amount to about 500 ml. The batch is then cooled down to −10° C. and acetylene (ca 4 l/min.) is regularly conducted into the acetylide suspension. After 5 minutes, the amount flowing through is reduced to 2 l/min. and after a further 15 minutes, it is adjusted to a minimum flowing velocity for a further 40 minutes in order to guarantee the saturation of the reaction solution with acetylene at −10° C.

EXAMPLE 2

A solution, pre-cooled to ca −20° C., of 100 g of 3-buten-2-one (purity 98.2%, water content ca 0.4%) in 100 ml of toluene is added within 45 minutes to a suspension of the monolithium acetylide-ammonia complex in toluene with continuous saturation of the reaction mixture with acetylene. After completed ketone addition, the mixture is left to react for 5 minutes.

Subsequently, the reaction mixture is allowed to flow while stirring within 20 minutes into 300 ml of 30% sulfuric acid so that the pH-value is always below 7 and the temperature during the hydrolysis does not rise above −5° C. The mixture is then adjusted with sodium hydroxide to a pH-value of 6.0–6.5, the neutralized solution is filtered and the filtrate is dried over sodium sulfate and distilled under vacuum up to the residue. There are obtained 1327.0 g of a 9.65% solution (according to GC with internal standard) of 3-methyl-4-penten-1-yn-3-ol in toluene and, after washing the filter residue with 500 ml of water, 12.9 g of a 6.45% extract from the water phasw. The filter residue contains 0.45 g of polymerisate; the distillation residue (also polymerisate) amounts to 5.6 g. Yield 95.5% (with respect to lithium 84.6%).

The suspension of the monolithium acetylide-ammonia complex in toluene is manufactured as follows:

500 ml of liquid ammonia are introduced into a reaction vessel with stirrer and reflux condenser (ca −70° C.) after a three-fold evacuation and replacement of the vacuum with nitrogen. While stirring at −35° C. there are dissolved within 20 minutes 11.0 g of lithium, and thereafter acetylene (4 l/min.) is conducted into the solution at the same temperature through an immersion tube. After about 15 minutes, a color change from blue-black to light grey (grey point) takes place. The acetylene introduction is continued for 5 minutes beyond the grey point. Thereafter, the temperature in the reflux condenser is regulated to ca −20° C. and ammonia is evaporated off within 3 hours. The distilled-off amount is continuously replaced by toluene (total 500 ml), so that the level in the reaction vessel during the ammonia-toluene exchange remains approximately constant. When the plateau temperature of ca 10° C. is reached, the mixture is furthermore heated with a mantle temperature of ca 20° C. until the internal temperature again begins to rise. After reaching the end temperature of ca 16 C., the batch is cooled down to 0° C. and ammonia is regularly conducted into the acetylide suspension for about 1 hour. The acetylene flow is adjusted at the beginning to about 4 l/min. and thereafter the acetylene uptake is adjusted so that the continuous saturation of the reaction mixture with acetylene is guaranteed.

EXAMPLE 3

A solution of 100 g of 4-(4-methoxy-2,3,6-trimethyl-phenyl)-3-buten-2-one (purity 95.5% in 174 ml of toluene is added regularly within 20 minutes to a suspension of the monolithium acetylide-ammonia complex in toluene. After completed ketone addition, the mixture is left to react for 30 minutes. The ketone addition and reaction period is carried out at 10° C. and with continuous saturation of the reaction mixture with acetylene.

Thereafter, the reaction mixture is allowed to flow into a neutralization vessel pre-cooled to ca $-10°$ C. By addition of 200 ml of ion-poor water within 5 minutes the batch is hydrolyzed and then adjusted to a pH-value of 6.5 by slow (about 20 minutes) dosing of ca 72 ml of glacial acetic acid. During the entire neutralization care is thereupon taken that the temperature does not rise above $-10°$ C. After separation of the water phase and evaporation of the solvent on a rotary evaporator under vacuum, there are obtained 110 g of crude product (purity: 94.0% according to GC with internal standard; distillation residue 5.1%) of 5-(4-methoxy-2,3,6-trimethylphenyl)-3-methyl-4-penten-1-yn-3-ol. Yield: 96.75%.

The suspension of the monolithium acetylide-ammonia complex in toluene is manufactured as follows;

250 ml of liquid ammonia are introduced into a reaction vessel with stirrer and reflux condenser (ca $-70°$ C.) after three-fold evacuation and replacement of the vacuum with nitrogen. While stirring at $-40°$ C. there are dissolved within 10 minutes 4.8 g of lithium, and thereafter acetylene (ca 4 l/min.) is, likewise at approximately $-40°$ C., conducted into the solution through an immersion tube. After about 10 minutes, a color change from blue-black to light grey (grey point) takes place. The acetylene introduction is continued for 5 minutes beyond the grey point. After completion of the acetylene introduction, the temperature in the reflux condenser is regulated to ca $-20°$ C., ammonia is evaporated off by heating with $2\frac{1}{2}$ hours and the distilled-off amount is continuously replaced by toluene (427 ml). When the plateau temperature of ca 10° C. is reached, the mixture is furthermore heated with a mantle temperature of ca 15° C., whereby simultaneously minimal acetylene is conducted into the actylide suspension for 1 hour. The internal temperature should thereby not exceed 10° C.

EXAMPLE 4

A solution of 100 g of beta-ionone (purity 96.8%) in 100 ml of diethyl ether is added dropwise within 30 minutes to a suspension of the monolithium acetylide-ammonia complex in diethyl ether at ca 0° C. and while saturating the reaction mixture with acetylene.

After a reaction time of 5 minutes at 0° C., the reaction mixture is poured within 5-10 minutes into a solution, pre-cooled to ca 0° C., of 45.6 g of glacial acetic acid in 200 ml of water and care is thereupon taken that the temperature does not exceed 0° C. The mixture is adjusted to a pH-value of 6.7-6.9 with ca. 50 ml of glacial acetic acid and the aqueous phase if separated in a separating funnel. The ether solution is dried over sodium sulfate, filtered and the residue is washed twice with 50 ml of diethyl ether. After the concentration of the combined ether solutions on the rotary evaporator up to constant weight, there are finally obtained 114.8 g of 94.6% (according to GC with internal standard) crude product of 3-methyl-5-(2,6,6,-trimethyl-1-cyclohexen-1-yl)-4-penten-1-yn-3-ol. Yield: 98.8%.

The suspension of the monolithium acetylide-ammonia complex in diethyl ether is manufactured as follows:

300 ml of liquid ammonia (dried over potassium hydroxide) are poured into a reaction vessel, pre-cooled to $-40°$ C., with stirrer and condenser (ca $-70°$ C.), while stirring at $-40°$ to $-35°$ C. within 10 minutes 4.4 g of lithium (purity 99%) are dissolved and thereafter the mixture is stirred for 5 minutes. Subsequently, at increased stirring speed, acetylene (ca 4 l/min.) is conducted into the solution through an immersion tube. After 8-9 minutes, a color change from blue-black to light grey (grey point) takes place. The acetylene introduction is continued for 5 minutes beyond the grey point and then the condenser is regulated to $-30°$ to $-20°$ C. Ammonia is evaporated off during ca 1 hour and the distilled-off amount is continuously replaced by diethyl ether. The end level is adjusted to 600 ml with diethyl ether. When the plateau temperature of ca 5° C. is reached, it is further heated with a mantle temperature of 20° C. until the internal temperature again rises. The end temperature should amount to 7.5°-8.0° C. Subsequently, the condenser is cooled down to $-70°$ C. and the reaction vessel is cooled down to $-5°$ C. and simultaneously acetylene (ca $2\frac{1}{2}$ l/min.) is conducted into the mixture for 5 minutes. Thereafter, the gas stream is reduced to $1\frac{1}{2}$ l/min. and after 15 minutes, the mixture is saturated with a minimal gas stream for 40 minutes.

EXAMPLE 5

The reaction of a solution of 99.54 g of 3-buten-2-one (purity 99.0%) in 100 ml of diethyl ether with a suspension of the monolithium acetylide-ammonia complex at $-10°$ C. and the subsequent hydrolysis are carried out analogously to Example 1. There are obtained 0.05 g of organic filter residue, 2.75 g of distillation residue and 129.5 g of 3-methyl-4-penten-1-yn-3-ol. Yield: 95.9% (based on lithium 90.0%).

The suspension of the monolithium acetylide-ammonia complex in diethyl ether is manufactured as follows:

500 ml of liquid ammonia are poured through a sodium hydroxide drying tower into a reaction flask with reflux condenser (ca $-70°$ C.) and while stirrying at $-40°$ C. within 20 minutes 10.5 g of lithium (purity 99%) are dissolved. Subsequently, there is conducted into the solution, likewise at $-40°$ C., through an immersion tube acetylene (ca 4 l/min.), which is previously passed through a washing flask with sulfuric acid. After the color change from blue-black to light grey, which takes place after about 15 minutes, acetylene is conducted in for a further 75 minutes, then the reflux condenser is removed, ammonia is evaporated off for about 1 hour and the distilled-off amount is continuously replaced by diethyl ether (total 660 ml). When the temperature in the reaction vessel has reached 5° C., the mixture is heated for a further 10 minutes with a mantle temperature of 15° C. The internal temperature thereby remains constant. Thereafter, the reflux condenser is adjusted to −20° C. and the ether-acetylide suspension is saturated with acetylene (ca 2 l/min.) for 20 minutes.

I claim:

1. A process for producing a compound of the formula:

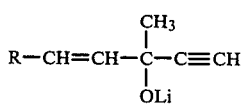

wherein R is hydrogen or an aliphatic or aromatic hydrocarbon which can be unsubstituted or substituted with lower alkoxy or lower alkyl groups comprising ethynylating by reacting acetylene, at a temperature of −30° to +30° C., with a ketone of the formula

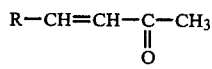

wherein R is as above in an inert organic solvent containing a suspension of a monolithium acetylide-ammonia complex composition.

2. The process of claim 1 wherein said ethynylation is carried out at a temperature of from about −20° to about 10° C.

3. The process of claim 1 wherein the ethynylation is carried out by continuously saturating the reaction medium with acetylene.

4. The process of claim 1 wherein toluene or diethyl ether is the inert organic solvent medium.

5. The process of claim 1 wherein R is hydrogen.

6. The process of claim 1 wherein R is 4-methoxy-2,3,6-trimethylphenyl.

7. The process of claim 1 wherein R is 2,6,6-trimethyl-1-cyclohexen-1-yl.

8. The process of claim 1 wherein said suspension contains from about 70% to about 120% equivalents of ammonia perequivalent of lithium.

9. A process for producing a tertiary acetylenic alcohol of the formula:

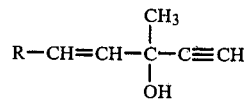

wherein R is hydrogen or an aliphatic or aromatic hydrocarbon comprising ethynylating by reacting acetylene, at a temperature of −30° to 30° C., with a ketone of the formula

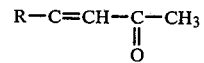

wherein R is as above in an inert organic solvent containing a suspension of a monolithium acetylide ammonia complex composition to produce a compound of the formula

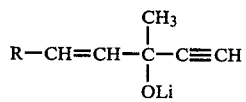

wherein R is as above and thereafter hydrolyzing said compound of formula II to produce said tertiary acetylenic alcohol.

10. The process of claim 9 wherein the ethynylation is carried out by continuously saturating the reaction medium with acetylene.

11. The process of claim 9 wherein toluene or diethyl ether is the inert organic solvent medium.

12. The process of claim 9 wherein R is hydrogen.

13. The process of claim 9 wherein R is 4-methoxy-2,3,6-trimethylphenyl.

14. The process of claim 9 wherein R is 2,6,6-trimethyl-1-cyclohexen-1-yl.

15. The process of claim 9 wherein said suspension contains from about 70% to about 120% equivalents of ammonia per equivalent of lithium.

* * * * *